US011473619B2

(12) United States Patent
Stich

(10) Patent No.: US 11,473,619 B2
(45) Date of Patent: Oct. 18, 2022

(54) DOUBLE-ROW ROLLING-ELEMENT BEARING UNIT HAVING PRELOADING ELEMENT

(71) Applicant: B. Braun Melsungen AG, Melsungen (DE)

(72) Inventor: Marcel Stich, Nieste (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 17/284,159

(22) PCT Filed: Oct. 10, 2019

(86) PCT No.: PCT/EP2019/077494
§ 371 (c)(1),
(2) Date: Apr. 9, 2021

(87) PCT Pub. No.: WO2020/074649
PCT Pub. Date: Apr. 16, 2020

(65) Prior Publication Data
US 2021/0332847 A1    Oct. 28, 2021

(30) Foreign Application Priority Data

Oct. 12, 2018  (DE) ..................... 10 2018 125 316.8

(51) Int. Cl.
*F16C 19/18*   (2006.01)
*F16C 25/06*   (2006.01)
(Continued)

(52) U.S. Cl.
CPC ............ *F16C 19/183* (2013.01); *F16C 19/56* (2013.01); *F16C 25/06* (2013.01); *F16C 25/083* (2013.01);
(Continued)

(58) Field of Classification Search
CPC .... F16C 19/181; F16C 19/182; F16C 19/183; F16C 19/56; F16C 25/06; F16C 25/083;
(Continued)

(56) References Cited

U.S. PATENT DOCUMENTS

| 4,647,230 A | 3/1987 | Friedrich et al. |
| 5,927,867 A | 7/1999 | Niebling et al. |

(Continued)

FOREIGN PATENT DOCUMENTS

| CN | 101253343 A | 8/2008 |
| CN | 104154116 A | 11/2014 |

(Continued)

OTHER PUBLICATIONS

Search Report received in German Application No. 10 2018 125 316.8 dated Jan. 18, 2019, with translation, 13 pages.

(Continued)

*Primary Examiner* — Phillip A Johnson
(74) *Attorney, Agent, or Firm* — Christopher A. Rothe; Cullhane Meadows, PLLC

(57) ABSTRACT

A double-row rolling-element bearing unit of a medical pump, preferably syringe pump, has a bearing core forming a first inner running surface for first rolling elements, which first inner running surface faces in an axial direction, and forms a second inner running surface for second rolling elements, which second inner running surface is arranged oppositely to the first inner running surface in the axial direction. The pump has a bearing bush, which can be mounted on a housing portion and forms a first outer running surface, which lies opposite the first inner running surface, and the pump has a bearing pan, which forms a second outer running surface, which lies opposite the second inner running surface. At least one preloading element couples the (Continued)

bearing pan to the bearing bush with a defined preload to join the double-row rolling-element bearing unit as a unit.

13 Claims, 5 Drawing Sheets

(51) Int. Cl.
    *F16C 33/58*     (2006.01)
    *F16C 33/60*     (2006.01)
    *F16C 19/56*     (2006.01)
    *F16C 25/08*     (2006.01)

(52) U.S. Cl.
    CPC .......... *F16C 33/586* (2013.01); *F16C 33/588* (2013.01); *F16C 33/60* (2013.01); *F16C 2226/74* (2013.01); *F16C 2316/10* (2013.01)

(58) Field of Classification Search
    CPC ...... F16C 33/586; F16C 33/588; F16C 33/60; F16C 33/605; F16C 2226/76; F16C 2316/10
    See application file for complete search history.

(56) References Cited

U.S. PATENT DOCUMENTS

| | | | |
|---|---|---|---|
| 6,227,715 | B1 | 5/2001 | Erhardt et al. |
| 6,269,711 | B1 | 8/2001 | Tejima |
| 10,107,330 | B2 | 10/2018 | Slavic |
| 2008/0279495 | A1 | 11/2008 | Schumacher et al. |
| 2010/0150490 | A1* | 6/2010 | Cymbal .................. F16C 19/00 384/585 |
| 2010/0284643 | A1 | 11/2010 | Nuissl et al. |
| 2014/0169719 | A1 | 6/2014 | Seufert et al. |
| 2014/0321780 | A1 | 10/2014 | Bussit et al. |

FOREIGN PATENT DOCUMENTS

| | | | | |
|---|---|---|---|---|
| CN | 105102835 | A | 11/2015 | |
| CN | 106460942 | A | 2/2017 | |
| DE | 924924 | C | 3/1955 | |
| DE | 2234984 | A1 | 2/1974 | |
| DE | 8009464 | U1 | 7/1980 | |
| DE | 3421188 | A1 | 12/1985 | |
| DE | 1971333 | A1 | 10/1998 | |
| DE | 102006034729 | B3 | 1/2008 | |
| DE | 102007019888 | A1 | 11/2008 | |
| DE | 102007044776 | A1 | 4/2009 | |
| DE | 102012215584 | A1 | 3/2014 | |
| DE | 102018204313 | A1 * | 9/2019 | ............ F16C 19/163 |
| DE | 102018112331 | A1 * | 11/2019 | |
| EP | 168791 | A1 | 1/1986 | |
| EP | 2908902 | A1 | 8/2015 | |
| FR | 437471 | A * | 4/1912 | |
| FR | 1350297 | A * | 1/1964 | |
| GB | 1257555 | A | 12/1971 | |
| GB | 1359028 | A | 7/1974 | |
| JP | 2005145173 | A | 6/2005 | |
| JP | 2007085559 | A | 4/2007 | |
| JP | 2008223776 | A | 9/2008 | |
| WO | 2014062160 | A1 | 4/2014 | |

OTHER PUBLICATIONS

International Search Report received in Application No. PCT/EP2019/077494 dated Jan. 14, 2020, with translation, 5 pages.
Written Opinion received in Application No. PCT/EP2019/077494 dated Jan. 14, 2020, with translation, 16 pages.
Written Opinion received in Application No. PCT/EP2019/077494 dated Jan. 14, 2020, with translation, 15 pages.

* cited by examiner

DOUBLE-ROW ROLLING-ELEMENT BEARING UNIT HAVING PRELOADING ELEMENT

CROSS-REFERENCE TO RELATED APPLICATION(S)

This application is the United States national phase entry of International Application No. PCT/EP2019/077494, filed Oct. 10, 2019, and claims the benefit of priority of German Application No. 10 2018 125 316.8, filed Oct. 12, 2018. The contents of International Application No. PCT/EP2019/077494 and German Application No. 10 2018 125 316.8 are incorporated by reference herein in their entireties.

FIELD

The present invention relates to a double-row roller bearing unit of a medical pump comprising a bearing core forming a first inner bearing surface facing in an axial direction for first rolling elements as well as a second inner bearing surface opposite to the first inner bearing surface in the axial direction for second rolling elements, a bearing sleeve attachable to a housing portion and forming a first outer bearing surface opposite to the first inner bearing surface, and a bearing pan forming a second outer bearing surface opposite to the second inner bearing surface. Furthermore, the present invention relates to a medical pump, preferably a syringe pump, having a corresponding double-row roller bearing unit.

BACKGROUND

Today, medical technology therapies require high-precision medical pumps, which have high requirements in terms of installation space, weight, operating and functional safety as well as accuracy, among other things. Accordingly, the individual mechanical components are subject to close tolerances, high miniaturization requirements and may have to be installed and adjusted in a complex manner.

For example, syringe pumps, such as the PERFUSOR® SPACE brand syringe pump by B.Braun, are frequently used in infusion therapy for the application of liquids which enable flexible, safe therapies and have to work with high precision in order to be able to accurately dose even minimal quantities of liquid. In such a syringe pump, a syringe filled with such a liquid is inserted into the pump and the syringe is then depleted at a defined delivery rate by a drive head (delivery operation), which is driven by a spindle. In this process, high axial loads are applied to the spindle at low rotational speeds over a long period of time, up to several days. If the syringe has to be changed, the drive head is retracted quickly, i.e. in a few seconds, at high rotational speeds and very low axial loads (reset operation). Due to the high accuracy requirements, correspondingly high requirements are placed on tolerances for the bearing arrangement of the spindle.

Currently, bearing concepts consisting of a large number of individual bearings are used for such precision applications. The components and assemblies required for the individual bearings have to be individually stored, commissioned and installed. The bearing arrangements are adjusted at great expense during assembly of the pump, which is made even more difficult by the fact that the available installation space is very limited and there are high miniaturization requirements. In particular, fastening of the bearing seats by means of screws is only possible to a limited extent or not at all due to the limited installation space of the pump. Accordingly, the assembly effort of the pump is high and cost-intensive and error-prone adjustment work is necessary, which makes a reproducibly precise installation of the bearing arrangements difficult. Furthermore, these bearing arrangements may have insufficient degrees of freedom of movement, which can result in jamming of the bearing arrangement, in particular during installation. In addition, the bearing concepts currently in use are subject to high friction.

SUMMARY

Accordingly, the object of the present invention is to overcome or reduce disadvantages known from the prior art, and in particular to make assembly of medical pumps simpler, safer, more precise and reproducible, and to reduce manufacturing costs.

The object underlying the invention is solved by a double-row roller bearing unit of a medical pump, preferably a syringe pump, having a bearing core which forms a first inner bearing surface, partly facing in an axial direction, for first rolling elements, and a second inner bearing surface, partly arranged opposite the first inner bearing surface in the axial direction, for second rolling elements. Furthermore, the pump has a bearing sleeve which can be attached to a housing portion or a bearing plate and forms a first outer bearing surface, opposite the first inner bearing surface, for the first rolling elements, and a bearing pan or bearing cover which forms a second outer bearing surface, opposite the second inner bearing surface, for the second rolling elements. Thereby, at least one pre-loading element is provided, which couples the bearing pan with the bearing sleeve with a defined pre-load/adjustment, in order to form the handleably pre-assembled, double-row roller bearing unit. Preferably, the pre-loaded roller bearing unit can be installed in the pump without pre-load adjustment.

In other words, an adjusted bearing arrangement is provided in X arrangement or O arrangement, which is provided by at least one pre-loading element as a pre-assembled and pre-loaded, clearance-free unit. In the context of the present invention, a bearing arrangement with an X arrangement means that two combined inclined bearing portions are arranged in mirror image to each other in such a way that pressure lines (directions along which forces are transmitted in a row of rolling elements) intersect in the corresponding bearing axis pointing in the direction of the respectively opposite row of rolling elements or the opposite inclined bearing portion. In an O arrangement, these pressure lines run in the opposite direction, i.e. in the direction radially inwards away from the opposite inclined bearing portion. Such a bearing arrangement enables very close, precise guidance of a shaft or spindle of the medical pump. Furthermore, the number of components required is significantly reduced compared with a conventional bearing arrangement, so that costs are reduced. Suitable rolling elements include, for example, cones, rollers or needles, and preferably balls, barrels and spherical rollers. In this context, the first and second rolling bearings can each be differently shaped and/or dimensioned depending on the loads that occur. The roller bearing unit is preferably lubricated for life.

Preferably, the bearing sleeve is attachable to the housing portion via a fitting portion, wherein the bearing pan is arranged along the axial direction adjacent to and not overlapping the fitting portion. In other words, in the assembled state of the bearing unit, the fitting portion and the bearing pan are preferably arranged offset from or spaced apart from each other along the axial direction. Further preferably, the at least one pre-loading element is an elastic portion of the bearing pan at least partially encompassing the bearing sleeve. In other words, the bearing pan and the pre-loading element are formed integrally. In particular, the bearing pan is slotted at its end facing the bearing sleeve, and webs remaining between the slots are elastically bendable in order to form several pre-loading elements. Advantages of this embodiment are that a radial installation space of the bearing unit can be reduced and/or the assembly of the same is simplified and/or the machining of the bearing seat is simpler and/or the at least one pre-loading element can be designed advantageously in terms of its bendability and handleability.

A roller bearing unit according to the invention makes it possible to significantly reduce the effort required for its installation in the pump and the associated preparation. Instead of several different bearings, the roller bearing unit can be transported, stored and commissioned as a single, preassembled assembly and can then be installed in the pump without having to provide a work step for adjusting the pre-load of the bearing. For example, the roller bearing unit can be pressed onto a shaft or spindle of a pump and can be secured to the pump housing via a fitting portion provided on either the bearing pan or bearing sleeve. Alternatively, the roller bearing unit can be glued, pressed or screwed into the pump housing, for example. For this purpose, a thread can be provided on an outer circumference of the roller bearing unit, for example.

Various designs of the at least one pre-loading element are also conceivable. It can be provided as a separate, elastic component, such as a tension or compression spring inserted in the roller bearing unit, or also as a group of separate, elastic components which are preferably arranged at equal distances around the circumference of the roller bearing unit. It is also conceivable to provide a threaded element provided on the bearing pan and/or the bearing sleeve as the pre-loading element and thus to brace the bearing pan and the bearing sleeve together by means of a screw thread, in particular an adjusting thread.

It has proven to be particularly practical that the at least one pre-loading element is at least one elastic portion of the bearing pan or bearing sleeve, preferably a number of snap hooks. Further preferably, a number of pre-loading elements is distributed at equal distances around the circumference of the bearing sleeve or bearing pan. Accordingly, this at least one pre-loading element at least partially surrounds or engages the bearing sleeve or bearing pan. Thus, the at least one pre-loading element is integrally connected to other components of the roller bearing unit, so that the number of components required can be reduced and the weight of the roller bearing unit can be optimized, and manufacturing costs can be reduced. In particular, the design of the pre-loading element as an elastic component that engages in/around another component, such as snap hooks, allows the pre-load of the roller bearing unit to be determined by this elasticity and a constructive design. Particularly due to the miniaturization of the roller bearing unit caused by the limited installation space, this is a considerable simplification. For example, compared with an adjustment via an adjusting thread, this has the advantage that preassembly of the rolling bearing unit is significantly faster and the high requirements for tolerances are reliably met, since the process is more reproducible, i.e. subject to fewer human errors. This significantly reduces manufacturing costs.

An advantageous embodiment of the roller bearing unit according to the invention provides that the first rolling elements and first bearing surfaces form a bearing arrangement in X-shape with the second rolling elements and second bearing surfaces. In particular, it is preferred that the first and/or second rolling elements allow wobbling motion of the bearing core relative to the bearing pan and the bearing sleeve (wobble-free operation), preferably in an angular range of +/−1° about the bearing axis or longitudinal axis.

A freedom to wobble is important in the roller bearing unit for the fastest, most reproducible and safest possible installation of the roller bearing unit according to the invention, since the shaft or spindle of the medical pump cannot usually be inserted perfectly coaxially with the bearing axis and/or with a bearing seat provided on the housing portion. During installation, in particular during handling of the spindle or shaft, minor angular deviations occur accordingly, which have to be allowed by the roller bearing unit. An X-shaped arrangement of the first and second rows of rolling bearings has a relatively large tilting clearance, i.e. it is suitable for allowing slight angular deviations between the bearing core and the bearing sleeve and bearing pan without jamming. Furthermore, according to this preferred embodiment of the invention, rounded rolling elements, i.e., barrels, spherical rollers or preferably balls are used to allow wobbling.

It is sensible for the bearing sleeve to form a flange projecting radially outwards, which is provided for support at the housing portion in a first load direction. Since the roller bearing unit is installed in such a way that the flange rests against the housing portion, the axial installation position of the roller bearing unit is determined by the flange. This is important for precise and reproducible installation of the roller bearing unit in the medical pump. In addition, the flange serves as a support for the axial forces transmitted from the roller bearing unit to the housing portion in the first load direction, which preferably corresponds to a main load direction, for example during delivery operation of the medical syringe pump.

Preferably, the roller bearing unit according to the invention is configured such that the at least one pre-loading element comprises one or more hold-down devices configured to rest against the housing portion radially outwards in order to press the at least one pre-loading element into an associated engagement contour when the double-row roller bearing is installed in the housing portion. This is advantageous in particular if snap hooks are provided as pre-loading elements, which at least partially engage around or into the bearing sleeve or bearing pan with a projection projecting radially inwards, wherein the snap hooks have to be bent up radially outwards during (pre-)assembly and disassembly of the roller bearing unit. The hold-down devices prevent the snap hooks from bending outwards when the roller bearing unit is installed in the pump, and thus serve as a self-locking device to prevent the bearing unit from opening during operation. This is advantageous in particular if the medical pump is a syringe pump with a traction spindle, since in such a pump high traction forces are applied to the roller bearing unit during delivery operation, which could cause the snap-on connection to open unintentionally.

Alternatively, it is conceivable to provide a hold-down device, in particular in the form of a circumferential projection or step projecting radially inwards on the housing portion, which presses from radially outside against the pre-loading elements or snap hooks. Depending on how the housing portion is structurally designed and to what requirements it is further subject, this solution is more cost-effective than the one in which the hold-down devices are formed by the pre-loading elements.

Furthermore, support elements are preferably formed on the roller bearing unit, projecting radially outwards and provided for support at the housing portion in a second load direction contrary to the first load direction. Expediently, the support elements are elastic in order to be able to deflect radially inwards. In particular, the second load direction is a secondary load direction in which forces act, for example, during a reset operation of the syringe pump. If both the flange and the support elements are provided, the roller bearing unit is secured axially in both directions in a form-fit manner. Support elements that can be sprung radially inwards simplify installation of the roller bearing unit in the pump, since they can be pushed out of the way. Furthermore, springback of the support elements can serve as a signal that the correct installation position has been reached.

In summary, it should be noted that the roller bearing unit according to the invention in its simplest form is provided with pre-loading elements. The support portions as well as the hold-down devices are advantageous configurations of the invention, which can be provided individually as well as in combination and, if necessary, formed in one piece, in order to achieve the advantageous effects described above.

The roller bearing unit is clearance-free and compact, its installation in the medical pump is very simple and reproducible, since no adjustment work or checking of the pre-load is necessary, and the unit costs are low, since the individual components of the roller bearing unit can be manufactured inexpensively by volume processes, such as injection molding from tribo-plastics. Likewise, the (pre-) assembly of the roller bearing unit itself, in particular in the snap-hook design, is fast, inexpensive and reproducible, since the components, in particular the snap hooks, are self-adjusting.

The roller bearing unit is preassembled by inserting the rolling elements, in particular balls, and the bearing core into the bearing sleeve or bearing housing and then tensioning them in a defined, clearance-free manner by attaching, in particular snapping on, the bearing pan or bearing cover. In the process, the bearing pan presses against the balls, which form a stop or limit to the pre-load path. Furthermore, when the bearing pan snaps on, the balls are pressed into their positions intended for operation or come to rest in their predetermined bearing surfaces/tracks. In particular, this forms a bearing element that is pre-loaded without X clearance. This means that the pre-load is achieved by mounting the roller bearing unit per se. The bearing pan, in particular in the snap-hook design, is resilient due to its shape and can be hooked into a detent geometry during assembly. This applies a permanent (pre-load) force to the rotatable inner rotor/bearing core. Both the assembly of the roller bearing unit itself and its installation in the pump can be easily automated.

Furthermore, the object underlying the invention is solved by a medical pump, preferably a syringe pump, which comprises a spindle, preferably a traction spindle, which is rotatably and axially fixed in a housing portion of the medical syringe pump by a double-row roller bearing unit according to the preceding description.

The preassembled roller bearing unit can be installed in the pump using a press-fit tool, which may be miniaturized. It is pressed into any intended bore with an appropriate fit. The strength of the connection is defined by the fit between the bore and the bearing unit and by the shear strength of a bearing collar (fitting portion).

BRIEF DESCRIPTION OF THE DRAWING FIGURES

The present invention is described below by means of exemplary embodiments with reference to the accompanying drawings, however, the invention is not to be limited thereto. The same reference signs are used for the same elements.

DETAILED DESCRIPTION

Figure 1:
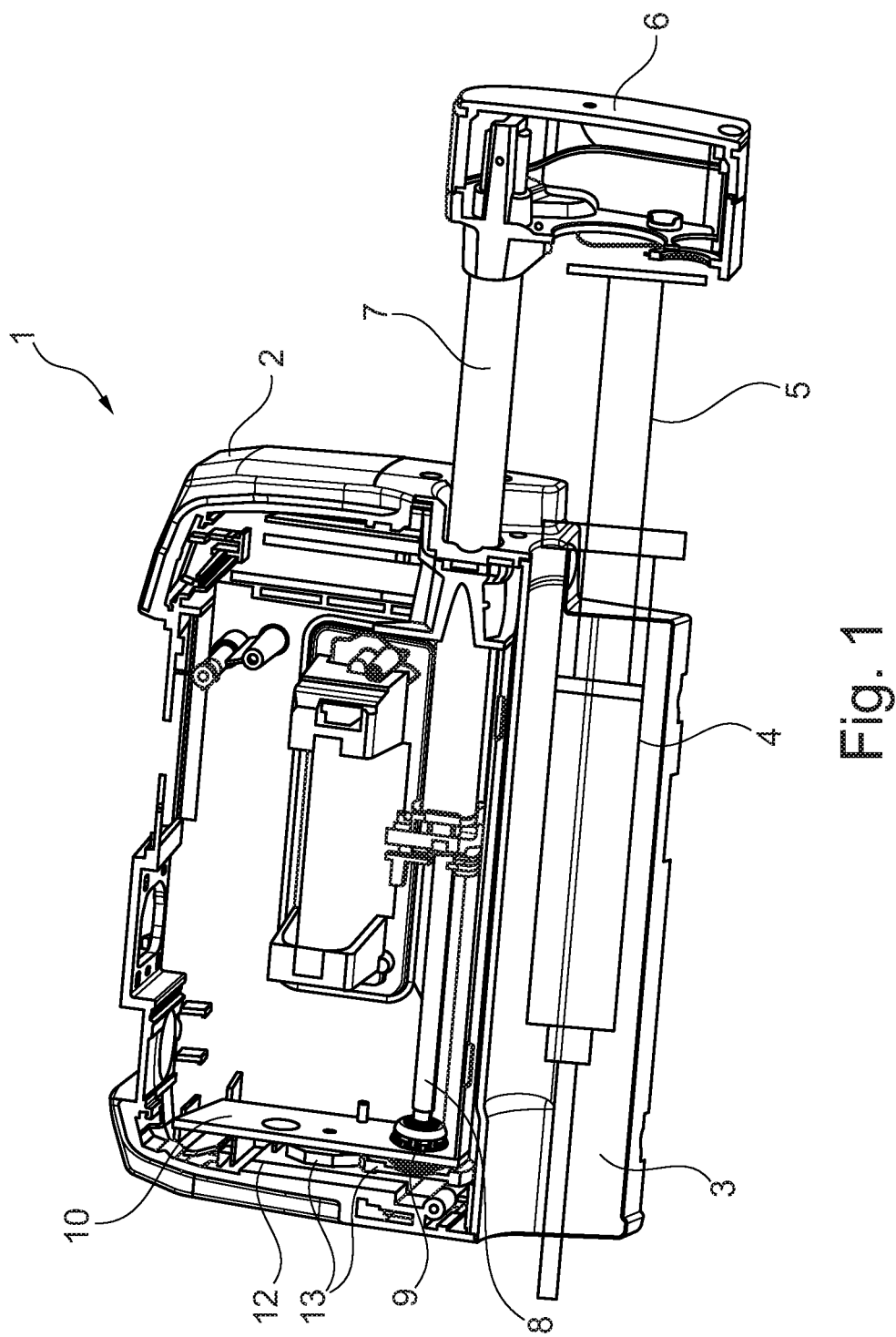
FIG. 1 shows a syringe pump in which a double-row roller bearing unit is installed in accordance with a first embodiment of the present invention.

The medical pump shown in FIG. 1 is a syringe pump 1 which is used, for example, in infusion therapy. The syringe pump 1 has a syringe housing 2 with a receiving compartment 3, which is used to house and, if necessary, hold a syringe 4 (indicated here schematically). During operation of the syringe pump 1, a syringe 4 filled with medication or the like is inserted into the receiving compartment 3 with a syringe plunger 5 for discharging the syringe 4 and rests against a drive head 6 of the syringe pump 1. The drive head 6 is axially displaceable in order to actuate the syringe plunger 5. To this end, it is connected to a spindle 8, or more precisely a traction spindle, via a drive tube 7 mounted so as to be axially displaceable on the syringe housing 2. A conversion mechanism (not shown) is provided between the drive tube 7 and the spindle 8, which converts a rotary movement of the spindle 8 into a longitudinal movement of the drive head 6.

In the following, for better orientation, the side of the syringe pump 1 and the roller bearing unit 9 facing in the direction of the drive head 6 or in a pulling direction will be referred to as the front side. The opposite side or direction of the syringe pump 1 and the roller bearing unit 9, which faces in the direction of the gear portion 12 or in a pushing direction, is referred to as the rear side.

The spindle 8 is rotatably and axially fixed to the syringe housing 2 by a double-row roller bearing unit 9. According to this embodiment, the double-row roller bearing unit 9 is seated in a bearing seat 11 formed by a bearing plate 10. The bearing plate 10 is a housing portion which serves to partition off a gear portion 12 in the syringe housing 2, in which drive gears 13 for driving the spindle 8 are arranged. The drive gears 13 are also mounted on the bearing plate 10. An electric motor (not shown) is further provided for driving the drive gears 13.

Figure 2:
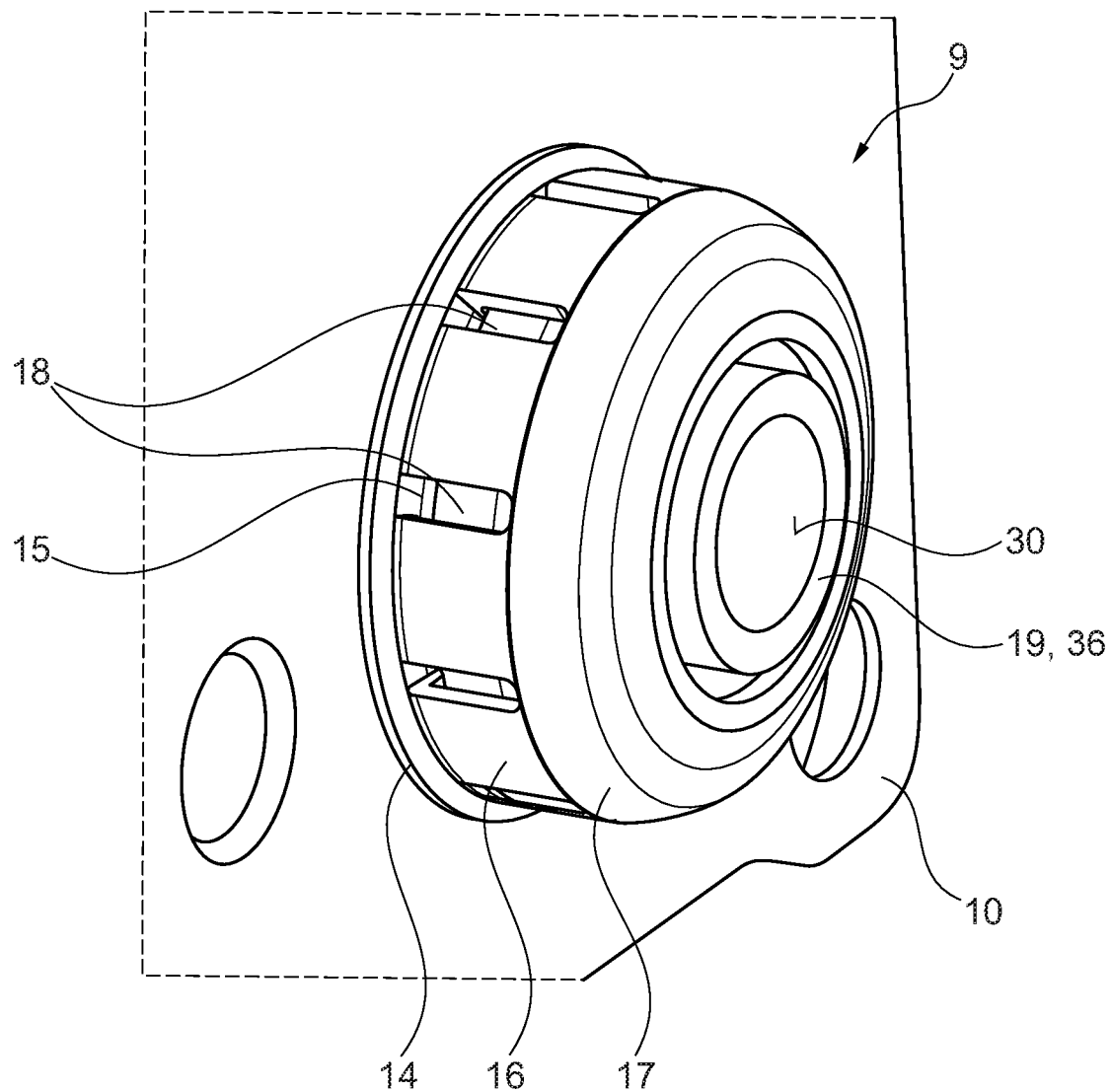
FIG. 2 shows a perspective view of the double-row roller bearing unit according to the first embodiment of the invention.

FIG. 2 is a perspective view of the double-row roller bearing unit 9. An outer bearing ring of the roller bearing unit 9 is made of two parts and has a bearing sleeve 14 and a bearing pan 17. The bearing sleeve 14 forms an engagement contour on the outside in the form of a circumferential groove 15, in which snap hooks 16 of the bearing pan 17 engage. The snap hooks 16 serve as a pre-loading element by which a defined pre-load/adjustment of the roller bearing unit 9 is generated. The snap hooks 16 are formed in that the bearing pan 17 has slots 18 distributed at equal distances around the bearing circumference at its rear end (i.e. facing the bearing plate 10 of the syringe housing 2 in the installed state), wherein the slots 18 run in the axial direction. Elastic webs, the snap hooks 16, remain between the slots 18. At its front end (i.e., facing away from the bearing plate 10 of the syringe housing when installed), the bearing pan 17 is curved radially inwards in a bowl-like manner and is open in the axial direction. A bearing core 19 is arranged within the bearing sleeve 14 and the bearing pan 17, the front end of which, as shown in FIG. 2, lies radially within an opening of the end of the bearing pan 17 facing away from the bearing plate 10. The roller bearing unit 9 is mounted to the bearing plate 10 as a preassembled assembly by pressing the bearing sleeve 14 into the bearing plate 10.

Figure 3:
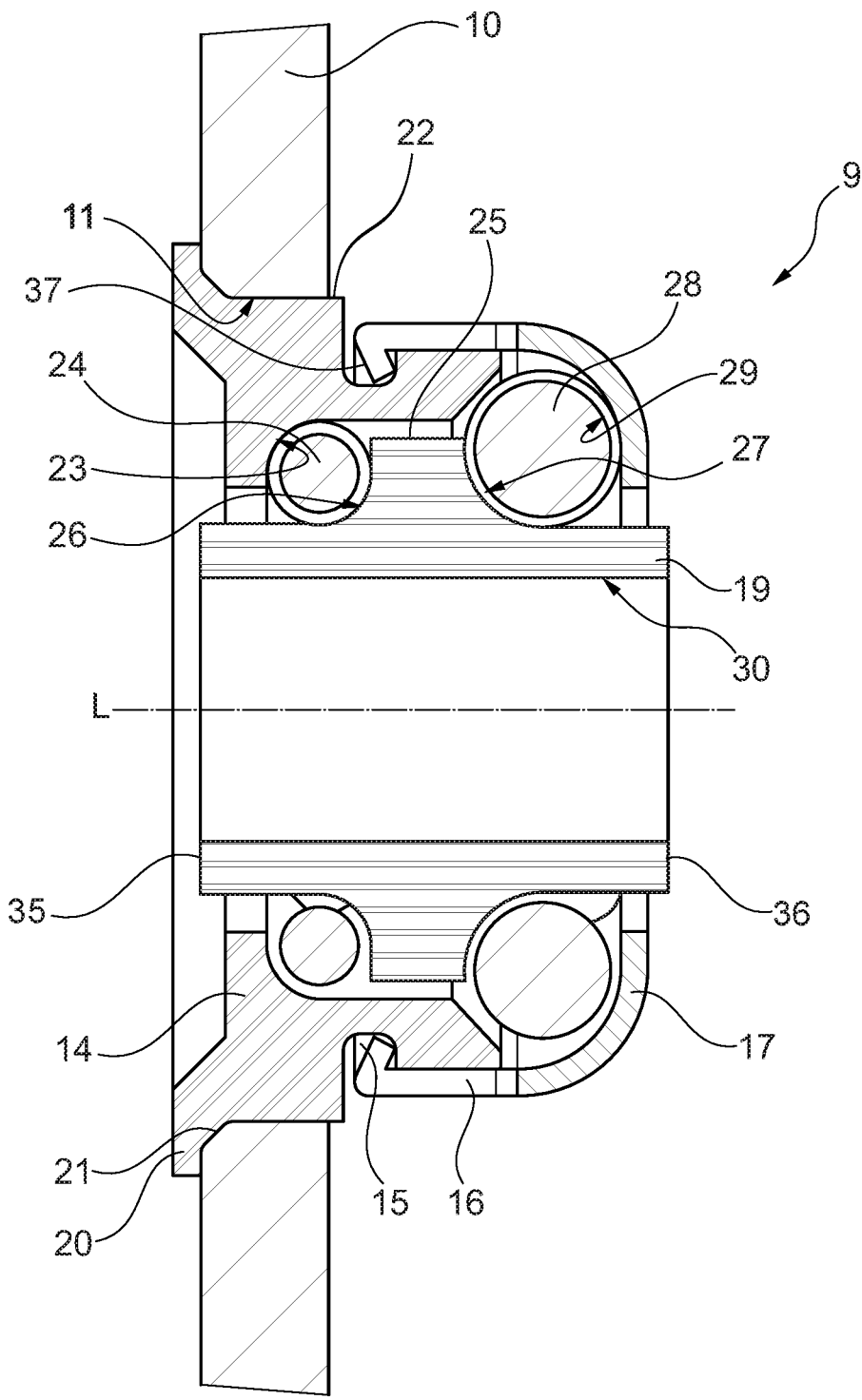
FIG. 3 shows a longitudinal sectional view of the double-row roller bearing unit according to the first embodiment of the invention.

FIG. 3 shows a longitudinal section of the roller bearing unit 9 according to the first embodiment. A position of the roller bearing unit 9 in the axial direction is determined by a collar or flange 20 formed by the bearing sleeve 14 and extending radially outwards abuts the bearing plate 10 on the rear side (i.e., on the side of the gear portion 12 or on the side facing away from the drive head 6). Furthermore, the flange 20 supports a tractive load acting on the spindle 8 during a delivery operation (i.e., a main load acting in the tractive direction toward the drive head 6) on the bearing plate 10. A chamfer 21 is provided around the bearing seat 11 at the rear side of the bearing plate 10 in order to facilitate press-fitting or installation of the bearing sleeve 14 to the bearing plate 10. Immediately at the front of the flange 20, the bearing sleeve 14 has a fitting portion 22 which extends in the axial direction and via which the bearing sleeve 14 is pressed into the bearing seat 11 formed by the bearing plate 10 as described above. Due to the press-fit connection created in this way, a compressive load acting on the spindle 8 (i.e., a secondary load acting in the direction of compression or in the direction of the rear side) is transmitted to the bearing plate 10. Immediately behind the fitting portion 22, the bearing sleeve 14 forms, in the following order, a step extending radially inwards, the circumferential groove 15, and an end portion extending in the axial direction toward the front.

On an inner side of the bearing sleeve 14, more precisely on a section of the bearing sleeve 14 lying radially inside the fitting portion 22 and the bearing seat 11, a collar extending radially inwards is provided, which forms a first outer bearing surface 23 of the type of an angular-contact groove ball bearing on its front side. The first outer bearing surface 23 supports first rolling elements 24, in this embodiment balls, on the rear side as well as radially on the outside.

Inside the bearing sleeve 14 is the bearing core 19, which is essentially sleeve-shaped and forms a spindle seat 30 on an inner circumferential surface for connection to the spindle 8. The spindle seat 30 is preferably a light clearance fit or transition fit, but may also be an interference fit. In a central region, the bearing core 19 further has a projection 25 projecting radially outwards. At a transition between the projection 25 and the rear end of the bearing core 19, a first inner bearing surface 26 of the type of an angular-contact groove ball bearing is formed for the first rolling elements 24, wherein the first inner bearing surface 26 faces the first outer bearing surface 23, diametrically opposite with respect to the rolling elements, in such a way that the first rolling elements 24 roll between the first inner bearing surface 26 and the first outer bearing surface 23 during a relative rotation of the bearing core 19 and the bearing sleeve 14.

At a transition of the projection 25 and the front end of the bearing core 19, a second inner bearing surface 27 of the type of an angular-contact groove ball bearing is formed in order to support second rolling elements 28, in this embodiment balls, on the rear side and radially on the inside. Facing the second inner bearing surface 27, diametrically opposite with respect to the rolling elements, a second outer bearing surface 29 of the type of an angular-contact groove ball bearing is formed on an inner side of the bearing pan 17, more precisely within its bowl-shaped end, in order to support the second rolling elements 28 on the front side as well as radially on the outside. That is, the second inner and second outer bearing surfaces 27, 29 face each other such that the second rolling elements 28 roll between the second inner bearing surface 27 and the second outer bearing surface 29 upon relative rotation of the bearing core 19 and the bearing pan 17.

Furthermore, it can be clearly seen in FIG. 3 that the snap hooks 16 formed by the bearing pan 17 engage in the circumferential groove 15 of the bearing sleeve 14 to thereby hold the roller bearing unit 9 together. Furthermore, it can be seen that the free ends of the snap hooks 16 which engage in the circumferential groove 15 are bent radially inwards and form a ramp or mounting inclination 37 at their rear end or rear end face, through which the snap hooks 16 come into contact with the bearing sleeve 14 during an assembly operation and are pressed or bent open towards the outside. More precisely, during an assembly of the roller bearing unit 9, the bearing core 19 and the rolling elements 24, 28 are inserted into the bearing sleeve 14 and the bearing pan 17 is pushed over the bearing sleeve 14 from the front side, wherein the snap hooks 16 meet the front end of the bearing sleeve 14 and are elastically bent outwards by the front mounting inclinations 37 until the snap hooks 16 finally snap into the circumferential groove 15 of the bearing sleeve 14. In the process, the snap hooks 16 cannot fully elastically reset themselves, but press against a front-side wall of the circumferential groove 15, whereby a defined pre-load or adjustment of the roller bearing unit 9 is achieved.

Furthermore, it can be seen in FIG. 3 that the step of the bearing sleeve 14 formed immediately behind the fitting portion 22 extends radially outwards beyond the outer circumference of the bearing pan 17, thereby shielding the snap hooks 16 in the axial direction. This prevents an interfering body from engaging behind the snap hooks 16, in particular in a preassembled, uninstalled state of the roller bearing unit 9, and unintentionally opening them, which would cause the roller bearing unit 9 to fall apart.

When a tensile load acts on the spindle 8, i.e., in a delivery operation of the syringe pump 1, a corresponding tensile force is transmitted to the bearing core 19 via the spindle seat 30 (in the case of interference fit of the spindle seat 30) or via the rear end face 35 (on the left in FIG. 3) of the bearing core 19 (in the case of clearance fit or transition fit of the spindle seat 30). For this purpose, it is advantageous if the bearing core 19 protrudes from an associated opening of the bearing sleeve 14. From the bearing core 19, the tensile force is transmitted via the second inner bearing surface 27 of the bearing core 19 to the second rolling elements 28 and from there to the second outer bearing surface 29 of the bearing pan 17. The tensile load thus acting on the bearing pan 17 is transmitted via the snap hooks 16 to the bearing sleeve 14 and from there via the friction in the press connection between the bearing sleeve 14 and the bearing plate 10 and via the flange 20 to the bearing plate 10. The flange 20 is required since relatively high forces act on the spindle 8 during the delivery operation. In the opposite operating direction, i.e. during a reset operation of the syringe pump 1, a comparatively low compressive load acts on the spindle 8, which is transmitted to the bearing core 19 via the spindle seat 30 or, if applicable, via a front end surface 36 (on the right in FIG. 3) of the bearing core 19. From there, the compressive load is transmitted via the first inner bearing surface 26 and the first rolling elements 24 to the first outer bearing surface 23 of the bearing sleeve 14 and from there to the bearing plate 10 via the friction in the press connection between the bearing plate 10 and the bearing sleeve 14. According to this embodiment, the first and second rolling elements 24, 28 are designed in accordance with the different loads in the tension and compression directions, so that smaller balls are selected for the first rolling elements 24 (e.g., with a diameter of 2 mm) than for the second rolling elements 28 (e.g., with a diameter of 3 mm).

Figure 4:
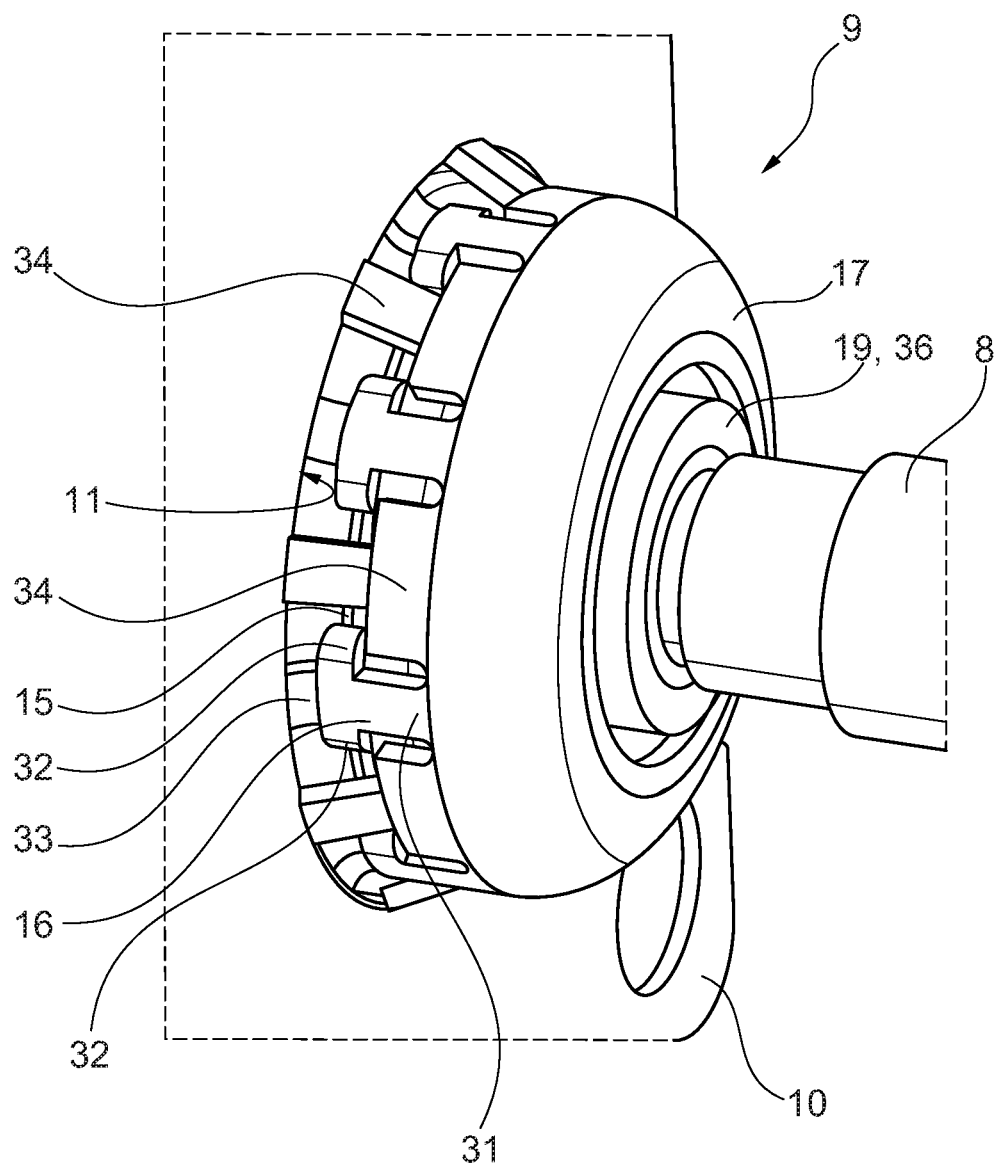
FIG. 4 shows a perspective view of the double-row roller bearing unit according to a second embodiment of the invention.

FIG. 4 shows a perspective view of a roller bearing unit 9 according to a second embodiment of the invention. The structure of the syringe pump 1, the roller bearing unit 9 itself and its installation situation correspond in large parts to those of the first embodiment, which is why only differences between the two embodiments are explained below in order to avoid redundant descriptions.

When comparing FIG. 4 with FIG. 2, it becomes clear that the greatest difference between the two embodiments lies in the design of the bearing pan 17, more precisely in the design of the sleeve-shaped section of the bearing pan 17 extending in the axial direction, which forms the pre-loading elements or snap hooks 16. The snap hooks 16 are distributed at uniform distances around the circumference of the bearing pan 17. According to this second embodiment shown in FIG. 4, the snap hooks 16 are formed from substantially cross-shaped sections of sheet metal, plastic or other elastically deformable materials (in particular of the same material and formed integrally with the rest of the bearing pan). The foot 31 of this cross is integrally connected to the bowl-shaped end of the bearing pan 17 and extends axially towards the bearing plate 10 or in the direction of compression. Two arms 32 of the cross extend on either side of the foot 31 in the circumferential direction or perpendicular thereto and are bent radially inwards with their free ends in order to engage in the circumferential groove 15. This connects the roller bearing unit 9 as a unit and provides pre-loading of the roller bearing unit 9. A head 33 of the cross is basically an extension of the foot 31 beyond the arms 32, and is bent radially outwards. The free end of the head 33 thereby abuts against an inner circumferential surface of the bearing seat 11 formed in the bearing plate 10, as a result of which the cross-shaped snap hooks 16 are elastically pressed radially inwards in the installed state or are at least held in the position engaging in the circumferential groove 15. That is, the head 33 of the cross serves as a hold-down device to secure the engagement of the arms 32 of the cross in the circumferential groove 15, whereby it can be prevented that they become disengaged even under a high tensile load.

In addition, the sleeve-shaped section of the bearing pan 17 extending in the axial direction forms elastic support elements 34. These are arranged around the circumference of the bearing pan 17 alternately with the snap hooks 16 at equal distances from each other. The support elements 34 are bent at an angle radially outwards in such a way that they are supported externally on the surface of the bearing plate 10 facing forwards, on the one hand in order to implement self-securing of the roller bearing unit 9 in the bearing plate 10 and, on the other hand, in order to transmit forces to the bearing plate 10 in a form-fitting manner in the direction of compression as well, instead of implementing this, as in the first embodiment, exclusively in a frictional manner via the press connection with the bearing seat 11.

Moreover, the support elements 34 are integrally connected to the bowl-shaped end of the bearing pan 17 via a widened base extending parallel to the bearing axis and further have a narrower free end connected to the base which is bent radially outwards as described above in order to rest against the bearing plate 10. In this regard, due to the manufacturing process, the base of a support element 34 lies between the feet 31 of two cross-shaped snap hooks 16 and the base ends just before two arms 32 of two snap hooks 16 in the axial direction. For example, this provides a simple, uniform cut width for inserting the snap hooks 16 and the support elements 34 into the integrally formed bearing pan 17. It should be noted that in this particular embodiment, both the snap hooks 16 and the support elements 34 are provided, but that they may also be provided individually and independently of each other.

Figure 5:
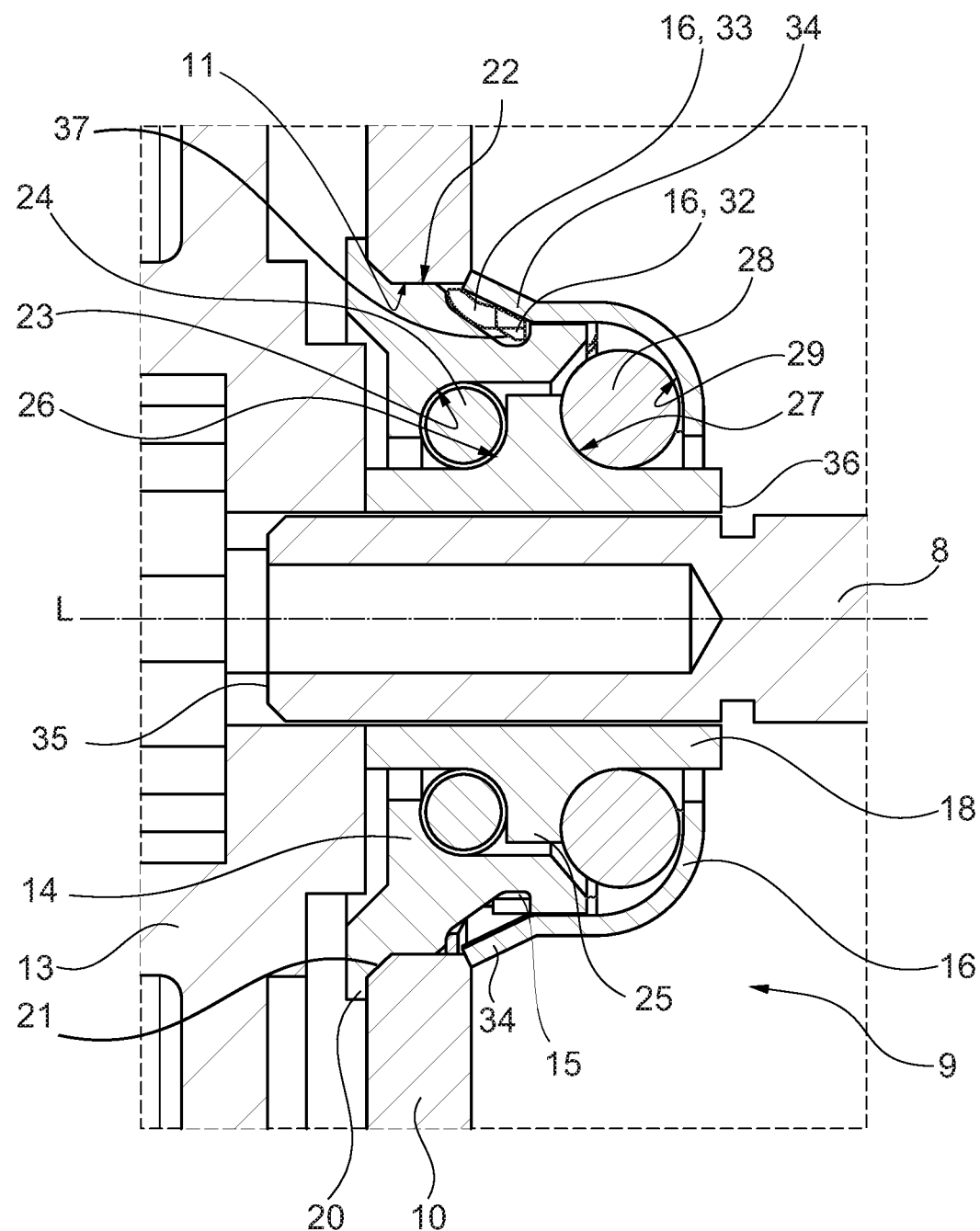
FIG. 5 shows a longitudinal sectional view of the double-row roller bearing unit according to the second embodiment of the invention.

FIG. 5 shows a longitudinal section through the roller bearing unit 9 of the second embodiment along a plane which runs through the bearing axis L and intersects diametrically opposite support elements 34 with respect to the roller bearing unit 9. In this view, it is readily apparent that the bearing plate 10 is slightly chamfered at the circumferential edge of the bearing seat 11 directed towards the front, in order to allow better support of the free ends of the support elements 34 on the bearing plate 10. By being elastic, the support elements 34 can deflect to allow the bearing to be fitted into the bearing seat 11 of the bearing plate 10 starting from the gear portion 12 side. In the end position, or when the installed state is reached, the support elements 34 leave the bearing seat 11 and deflect outwards to provide axial support against the bearing plate 10.

Furthermore, a snap hook 16 is visible behind one of the support portions 34 (located at the top in FIG. 5), wherein the head 33 of the snap hook 16 is supported in the radial direction against the inner circumferential surface of the bearing seat 11 of the bearing plate 10. It is also readily apparent that the fitting portion 22 of the bearing sleeve 14 is relatively short compared to that of the first embodiment and does not extend in the axial direction beyond the bearing seat 11 of the bearing plate 10, so that a portion of the bearing seat 11 is exposed, against which the heads 33 of the snap hooks 16 can rest. Furthermore, an arm 32 of the snap hook 16 can be seen, which engages in the circumferential groove 15 of the bearing sleeve 14 and also forms a ramp or mounting inclination 37 on its rear end face, via which the snap hook 16 is pressed radially outwards when the bearing pan 17 snaps onto the bearing sleeve 14.

In other words, in the second embodiment, the geometry of the bearing pan 9 is extended in such a way that, after being pressed into the bearing seat 11, retaining tabs or support elements 34 snap into place and secure the bearing also in the direction of compression by form fit and not only by frictional engagement, as in the first embodiment. In addition, the hold-down devices 33 prevent the latching geometries (snap hooks 16) on the bearing pan 17 from opening under tensile forces Z.

FIG. 4 and FIG. 5 also show the roller bearing unit 9, to which both the spindle 8 and one of the drive gears 13 are already attached. This installation situation is equally transferable to the first embodiment.

The roller bearing unit 9 according to the first embodiment described above is particularly simple and inexpensive and is advantageous in particular in the case of relatively low loads. However, if the roller bearing unit 9 is subjected to higher loads, then the roller bearing unit 9 according to the second embodiment described above may be advantageous, since this has additional securing means and fastenings in the form of the hold-down devices 33 and support elements 34 in order to absorb higher loads without increasing the number of components required, the effort of (pre-)assembly or of the installation of the roller bearing unit 9 according to the invention in the syringe pump 1.

The invention claimed is:

1. A double-row roller bearing unit for supporting movable, rotating components of a medical pump, the double-row roller bearing unit comprising:
   a bearing core which forms a first inner bearing surface, partially facing in an axial direction, for first rolling elements and a second inner bearing surface, partially arranged opposite the first inner bearing surface in the axial direction, for second rolling elements;
   a bearing sleeve attachable to a housing portion and forming a first outer bearing surface, opposite the first inner bearing surface, for the first rolling elements;
   a bearing pan forming a second outer bearing surface, opposite the second inner bearing surface, for the second rolling elements; and
   at least one pre-loading element which couples the bearing pan to the bearing sleeve with a defined pre-load in order to form the double-row roller bearing unit, wherein the at least one pre-loading element is an elastic portion of the bearing pan or of the bearing sleeve which correspondingly at least partially embraces or engages the bearing sleeve or respectively the bearing pan,
   wherein the at least one pre-loading element comprises one or more hold-down devices configured to rest against the housing portion radially outwards in order to press the at least one pre-loading element into an associated engagement contour when the double-row roller bearing unit is installed in the housing portion, and
   support elements projecting radially outwards are provided for support at the housing portion in a first axial load direction and which are elastic in order to be able to deflect radially inwards.

2. The double-row roller bearing unit according to claim 1, wherein the double-row roller bearing unit is configured to be installed in the pump without pre-load adjustment.

3. The double-row roller bearing unit according to claim 1, wherein the elastic portion of the bearing pan or of the bearing sleeve comprises snap hooks.

4. The double-row roller bearing unit according to claim 1, wherein the first rolling elements and the first inner and outer bearing surfaces form an X-arranged bearing arrangement with the second rolling elements and the second inner and outer bearing surfaces.

5. The double-row roller bearing unit according to claim 1, wherein the first and/or second rolling elements allow a wobbling movement of the bearing core relative to the bearing pan and the bearing sleeve.

6. The double-row roller bearing unit according to claim 1, wherein the bearing sleeve forms a flange projecting radially outwards which is provided for support at the housing portion in a second axial load direction.

7. A medical pump having a spindle that is mounted rotatably and axially fixed in a housing portion of the medical pump by the double-row roller bearing unit according to claim 1.

8. The medical pump according to claim 7, wherein the spindle is operable in a secondary load direction corresponding to the first axial load direction and in a main load direction.

9. The medical pump according to claim 7, wherein an angle of the end face of the free end of the support elements corresponds to an angle of an inclined surface of the housing portion and abuts the inclined surface.

10. The double-row roller bearing unit according to claim 1, wherein the bearing pan forms the support elements.

11. The double-row roller bearing unit according to claim 1, wherein the support elements are arranged around the bearing pan in alternation with the at least one pre-loading element.

12. The double-row roller bearing unit according to claim 1, wherein the support elements are bent obliquely radially outwards.

13. The double-row roller bearing unit according to claim 1, wherein a free end of the support elements has an end face extending obliquely to a bearing axis.

* * * * *